United States Patent [19]
Hopkins

[11] 3,994,557
[45] Nov. 30, 1976

[54] OPTICAL SYSTEMS

[75] Inventor: Harold Horace Hopkins, Reading, England

[73] Assignee: The Secretary of State for Social Services in Her Brittanic Majesty's Government of the United Kingdom of Great Britain and Northern Ireland, London, England

[22] Filed: Feb. 19, 1975

[21] Appl. No.: 551,063

[30] Foreign Application Priority Data
Feb. 20, 1974 United Kingdom............... 7815/74

[52] U.S. Cl. .................................. 350/33; 350/52; 128/4
[51] Int. Cl.² .................... G02B 23/00; A61B 1/00
[58] Field of Search ............... 350/33, 48, 50, 52, 350/54, 301, 96 R; 128/4–10, 27, 22

[56] References Cited
UNITED STATES PATENTS

| | | | |
|---|---|---|---|
| 1,551,770 | 9/1925 | Palmeter | 350/33 |
| 2,857,523 | 10/1958 | Corso | 350/33 |
| 3,450,457 | 6/1969 | Clave et al. | 350/52 |

FOREIGN PATENTS OR APPLICATIONS

| | | | |
|---|---|---|---|
| 769,444 | 3/1957 | United Kingdom | 350/52 |

OTHER PUBLICATIONS

Pearson, *Nat'l Photographer*, Aug. 1942, p. 17–19.

Primary Examiner—John K. Corbin
Assistant Examiner—Jon W. Henry
Attorney, Agent, or Firm—Cameron, Kerkam, Sutton, Stowell & Stowell

[57] ABSTRACT

A dual viewing optical system, for attachment to an optical instrument, having beam splitting means which can provide first and second beams of light, a first viewing position at which the first beam can be viewed, attached to the beam splitting means a first tube along which the second beam can pass, the said first tube having a coaxial joint which allows coaxial relative rotation of the ends of the tube, a remote eye piece attached to the end of said tube remote from the beam splitting means by a first swivel joint which can rotate about an axis perpendicular to the axis of the tube and allow the axial length of the remote eye piece to be pivoted about said axis of the swivel joint in a plane parallel to but displaced from the axis of the said tube, whereby the remote eye piece may lie in any spatial direction relative to the direction of the first beam, and optical means to relay the second beam to the remote eye piece.

16 Claims, 4 Drawing Figures

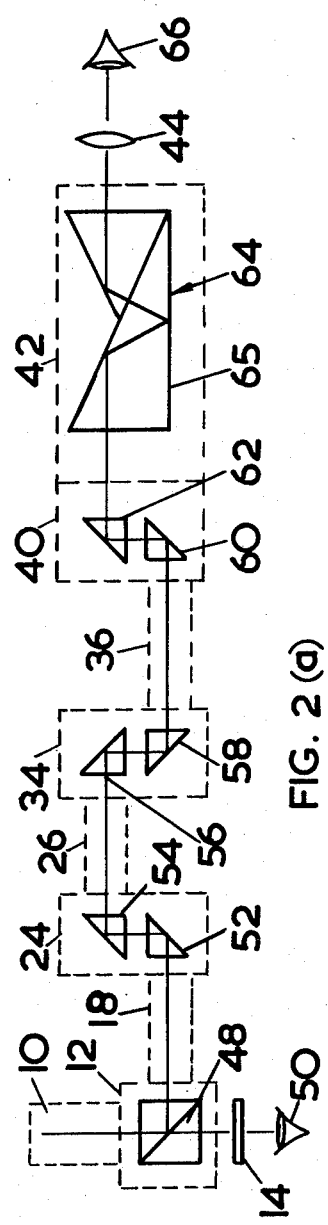
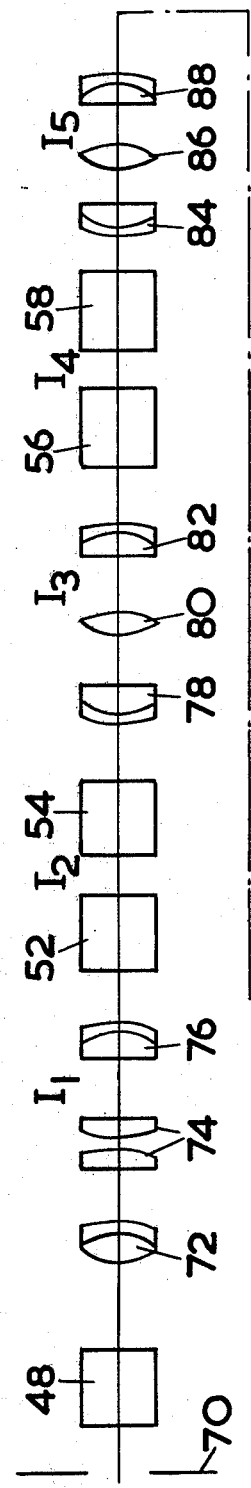
FIG. 2(a)
FIG. 2(b)

OPTICAL SYSTEMS

This invention relates to optical systems, particularly to systems by which identical views of an object are provided at two different positions. Such a system will be referred to in this specification as a dual viewing system.

One particular instrument with which such a system can be advantageously used is an endoscope, i.e. an instrument for viewing long, narrow body cavities, such as a cystoscope used to view a bladder. Delicate manipulation is required to obtain a required view and, as soon as the operator ceases viewing, the endoscope may be moved slightly and a different view obtained. This can be troublesome during instruction of students or when a photographic record is needed.

It is an important requirement that any attachment to the endoscope be flexible so that substantially no force is transmitted from it to the endoscope itself.

Previously, endoscopes have been provided with a dual viewing system incorporating beam splitting means and fibre optics, but the usual problems associated with fibre optics, that is, loss of detail in the image, and mismatch if more than one bundle of fibre is used consecutively, are undesirable in a precision aid to surgery.

According to the invention a dual viewing optical system as hereinbefore defined for attachment to an optical instrument, comprises a beam splitting means which can provide first and second beams of light, a first viewing position at which the first beam can be viewed, attached to the beam splitting means a first tube along which the second beam can pass, the said first tube having a coaxial joint which allows coaxial relative rotation of the ends of the tube, a remote eyepiece attached to the end of the said tube remote from the beam splitting means by a first swivel joint which can rotate about an axis perpendicular to the axis of the tube and allow the axial length of the remote eyepiece to be pivoted about said axis of the swivel joint in a plane parallel to but displaced from the axis of the said tube, whereby the remote eyepiece may lie in any spatial direction relative to the direction of the first beam, and optical means to relay the second beam to the remote eyepiece.

There may be provided additionally between the swivel joint and the remote eyepiece a second tube having a coaxial joint and a second swivel joint in series, the second swivel joint allowing the axial length of the second tube to pivot about the swivel joint in a plane parallel to but displaced from the axis of the first tube.

Preferably there are provided between the swivel joint and the remote eyepiece a second tube, a second swivel joint, a third tube and a third swivel joint, each tube having a coaxial joint.

The optical means to relay the second beam may be a lens or plurality of lenses in the tube, or each tube, and reflecting means in the form of two reflecting surfaces such as two parallel mirrors or two reflecting prisms in each swivel joint arranged to reflect the beam passing axially along the preceding tube so as to pass axially along the succeeding tube or remote eyepiece. When three tubes are provided the lenses are conveniently arranged to give a telescopic system in each tube with an image at infinity in each swivel joint between the two reflecting means. The lenses may be arranged so that the telescopic system in the first tube has an angular magnification of less than one, for example ½, the telescopic system in the second tube has an angular magnification numerically equal to 1, for example −1, and the optical means in the third tube has an angular magnification numerically greater than one and preferably equal to the reciprocal of the angular magnification in the first tube, for example 2. With such an arrangement the overall magnification is numerically one, and an observer at the remote eyepiece sees an image of the same size as that at the first viewing position; preferably the images are also arranged to be congruent. At the first viewing position the first beam may be viewed directly or, if required, magnifying means may be provided.

The system is not restricted to the case in which light is parallel at each swivel joint. The swivel joint may be located anywhere along the optical path where the presence of lenses would not preclude such location. The optical system may be arranged so as to be piecewise telescopic; that is, in parts each of which receiving parallel light will give out parallel light along the optical axis. A number of arrangements are possible which come within this requirement; for example, the optical system can be arranged to provide a focused image at one or more of the swivel joints.

A dual viewing system according to the invention may be used in conjunction with an endoscope, such as a cystoscope, which is arranged to provide a required image at the beam splitting means. Usually an endoscope provides an image at infinity.

An image rotating prism may be provided adjacent to the remote eyepiece so that the image can be rotated about the optical axis. This allows initial angular correlation of the images at the first viewing position and the remote eyepiece and also allows small alterations to be made to correct for rotations introduced into the image at the remote eyepiece as the configuration of the coaxial and swivel joints alters while the apparatus is in use.

Preferably the lenses of the remote eyepiece and those of the tube terminating in that eyepiece are arranged so as to avoid, at least in part, any errors of astigmatism and image curvature introduced by the lenses in the tubes.

The invention will now be described by way of example only with reference to the drawings filed with the specification in which:-

FIG. 2a illustrates schematically part of the opticl arrangement of the same dual viewing system; and FIG. 2b is a developed diagram of FIG. 2a;

Figure 1:
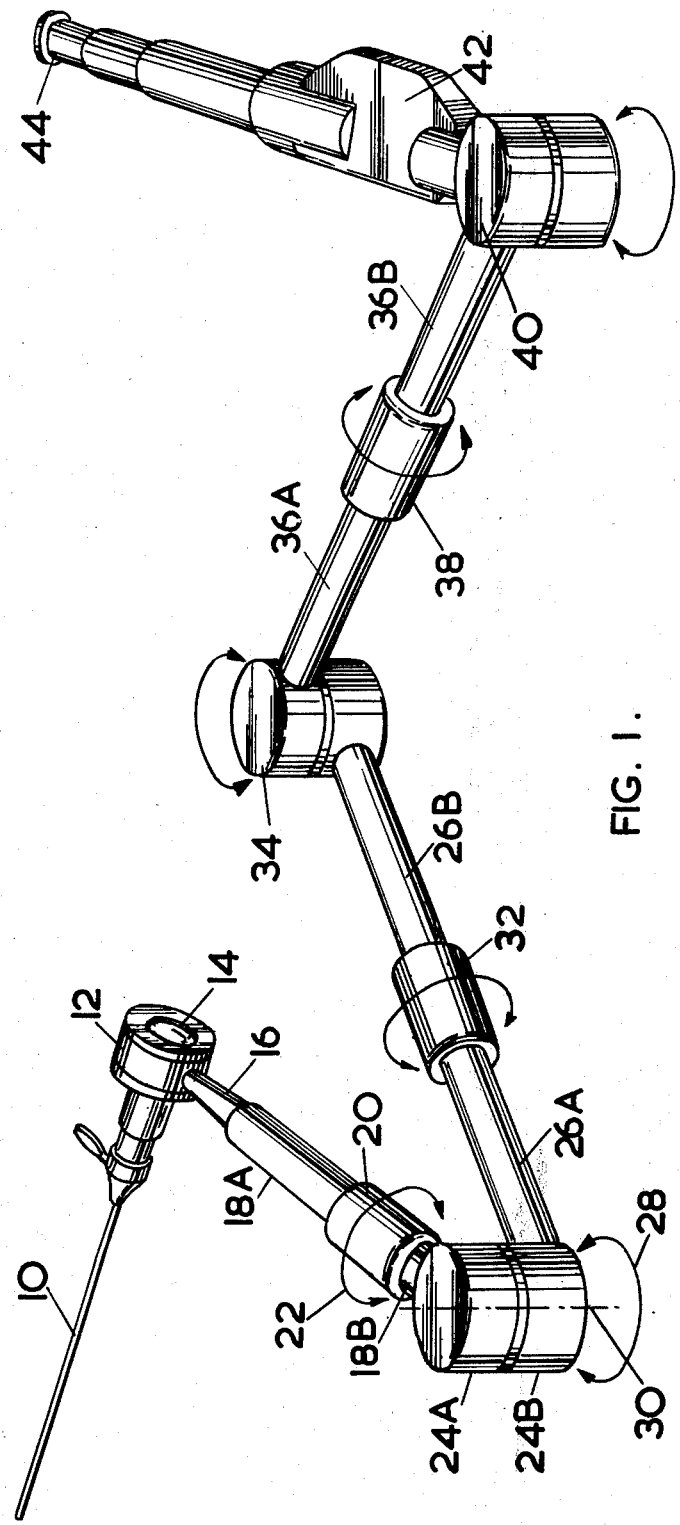
FIG. 1 shows a dual viewing system according to the invention in conjunction with a cystoscope.

In FIG. 1, a conventional cystoscope shown fragmentarily at 10 is connected at its proximal end to an enclosure 12 containing a beam splitting prism (see FIG. 2). The enclosure 12 is provided with a viewing window 14 at a first viewing position and with hollow shank 16 connected to a first tube 18 which is provided in two coaxial portions 18A, 18B connected by a coaxial joint 20, the joint allowing relative coaxial rotation of portions 18A, 18B as indicated by the arrow 22. The tube portion 18B is connected to a first part 24A of a swivel joint 24, the joint having a second part 24B connected to a second tube 26. The swivel joint 24 allows relative pivoting of the tubes 18 and 26 in the direction shown by the arrow 28, the axes of tubes 18 and 26 lying in parallel displaced planes which are perpendicular to the axis 30 of the swivel joint 24.

Similarly the second tube 26A, 26B contains a coaxial joint 32 and is connected through a swivel joint 34 to a third tube 36A, 36B which has a coaxial joint 38 and which is connected through a swivel joint 40 to an enclosure 42 containing an image rotating prism (see FIG. 2). The coaxial joints 32, 38 and swivel joints 34, 40, allow rotation in the directions shown by the respective arrows. To the enclosure 42 is connected a remote eyepiece 44 which is conveniently adjustable to allow focussing.

The rotations of the coaxial and swivel joints allow the second eyepiece 44 to lie in any direction in space relative to the first beam and to the cystoscope 10 with transmission of substantially no force to the cystoscope 10.

In FIG. 2a the direction of an axial beam of light is shown. The enclosure 12 contains a beam splitting prism 48 from which a first beam of light can pass to an observer 50 at the viewing window 14 and a second beam can pass through the tube 18 to two reflecting prisms 52, 54, one contained in each part of the swivel joint 24. The second beam passing axially along the tube 18 is reflected by the prisms 52, 54 to pass axially along the tube 26 in a plane parallel to the plane in which the tube 18 lies. Similarly the beam is reflected by prisms 56, 58 in swivel joint 34 to pass along the tube 36, and by prisms 60, 62 in the swivel joint 40 to pass to the image rotating prism 64, here shown as a K prism. The beam can pass from the prism 64 to an observer 66 at the remote eyepiece 44.

The arrangement of the prisms in the swivel joints is such that an image is relayed through the system whatever the relative orientations of the tubes 18, 26 and 36.

In the system, there are an even number of reflections so that the images seen by observers 50 and 66 are congruent.

The image rotating prism 64 allows orientation of the image presented to the observer 66 about the axis of the second beam, thus allowing the directions of the images presented to the observers 50 and 66 to be correlated initially. Also, movement of the tubes 18, 26 and 36 while the dual viewing system is in use may cause slight rotations of the image at the remote eyepiece, and the second observer can correct the angle if necessary.

For simplicity, not all of the optical means required to transfer an image from the beam splitting prism 48 to the remote eyepiece 44 are included in FIG. 2a. Each of the tubes 18, 26 and 36 contains several lenses forming a telescopic system, and one example of a suitable combination of lenses is shown in FIG. 2b, which is not to scale.

In the Figure, the exit pupil of the endoscope is represented by reference 70 and is adjacent to the beam splitter 48. Objective lens 72 and field lens 74 form an intermediate image of the exit pupil at $I_1$. Light then passes through the relay lens 76 and reflecting prism 52 and an image at infinity is formed in the space between the prisms 52 and 54 in swivel joint 28 as indicated by reference $I_2$. The lenses 72, 74 and 76 are contained in tube 18.

Similarly, the tube 26 contains objective lens 78 and a field lens 80 which form an intermediate image at $I_3$. Objective lens 82 forms an image at infinity in the space between prisms 56 and 58 ($I_4$). The tube 36 contains objective lens 84 and a field lens 86 which form an intermediate image at $I_5$, and objective lens 88 forms an image at infinity in the space between prisms 60 and 62 ($I_6$). This image is relayed through the image rotating prism 64 and relay lens 90, and an intermediate image is formed at $I_7$, and is focussed by eyepiece lenses 92, 94 adjacent to the second observer.

All of the lenses are triple layer coated to reduce light loss, the entry and exit surfaces of the K prism 64 are also triple coated, and the reflecting surface 65 is metallised.

The lenses in tubes 18, 26 and 36 are all positive and the cumulative errors of astigmatism and field curvature are to some extent corrected by the lenses 90, 92, 94 in the eyepiece 44. The full specification of the optical system is given in Table I.

TABLE I

| Component | c(mm⁻¹) | d(mm) | n | v |
| --- | --- | --- | --- | --- |
| Beam Splitter 48 | 0.0 | | | |
| | | 6.0 | 1.51872 | 0.00811 |
| | 0.0 | | | |
| Objective lens 72 | 0.032932 | | | |
| | | 2.5 | 1.51872 | 0.00811 |
| | −0.048088 | | | |
| | | 1.0 | 1.65222 | 0.019412 |
| | −0.014554 | | | |
| | | 43.1838 | 1 | 0 |
| Field lenses 74 | 0.0 | | | |
| | | 2.0 | 1.51872 | 0.00811 |
| | −0.024886 | | | |
| | | 0.5 | 1 | 0 |
| | 0.024886 | | | |
| | | 2.0 | 1.51872 | 0.00811 |
| | 0.0 | | | |
| | | 98.2107 | 1 | 0 |
| Objective lens 76 | −0.000463 | | | |
| | | 2.75 | 1.57487 | 0.010038 |
| | −0.043098 | | | |
| | | 1.5 | 1.65222 | 0.019412 |
| | −0.02084 | | | |
| | | 6.07411 | 1 | 0 |
| Reflecting Prism 52 | 0.0 | | | |
| | | 16.0 | 1.51872 | 0.00811 |
| | 0.0 | | | |

TABLE I-continued

| Component | c(mm⁻¹) | d(mm) | n | v |
|---|---|---|---|---|
| | | 16.0 | 1 | 0 |
| Reflecting Prism 54 | 0.0 | | | |
| | | 16.0 | 1.51872 | 0.00811 |
| | 0.0 | | | |
| | | 5.5317 | 1 | 0 |
| Objective lens 78 | 0.02084 | | | |
| | | 1.5 | 1.65222 | 0.019412 |
| | 0.043098 | | | |
| | | 2.75 | 1.57487 | 0.010038 |
| | 0.000463 | | | |
| | | 93.9051 | 1 | 0 |
| Field lens 80 | 0.014834 | | | |
| | | 2.0 | 1.51872 | 0.00811 |
| | −0.014834 | | | |
| | | 97.8483 | 1 | 0 |
| Objective lens 82 | −0.000463 | | | |
| | | 2.75 | 1.57487 | 0.010038 |
| | −0.043098 | | | |
| | | 1.5 | 1.65222 | 0.019412 |
| | −0.02084 | | | |
| | | 5.53172 | 1 | 0 |
| Reflecting prism 56 | 0.0 | | | |
| | | 16.0 | 1.51872 | 0.00811 |
| | 0.0 | | | |
| | | 16.0 | 1 | 0 |
| Reflecting prism 58 | 0.0 | | | |
| | | 16.0 | 1.51872 | 0.00811 |
| | 0.0 | | | |
| | | 4.547 | 1 | 0 |
| Objective lens 84 | 0.02084 | | | |
| | | 1.5 | 1.65222 | 0.019412 |
| | 0.043098 | | | |
| | | 2.75 | 1.57487 | 0.010038 |
| | 0.000463 | | | |
| | | 93.9051 | 1 | 0 |
| Field lens 86 | 0.014834 | | | |
| | | 2.0 | 1.51872 | 0.00811 |
| | −0.014834 | | | |
| | | 99.8298 | 1 | 0 |
| Objective lens 88 | 0.013243 | | | |
| | | 2.75 | 1.52611 | 0.008925 |
| | −0.040161 | | | |
| | | 1.5 | 1.60923 | 0.01613 |
| | −0.010604 | | | |
| | | 4.5175 | 1 | 0 |
| Reflecting prism 60 | 0.0 | | | |
| | | 16.0 | 1.51872 | 0.00811 |
| | 0.0 | | | |
| | | 8.0 | 1 | 0 |
| Reflecting prism 62 | 0.0 | | | |
| | | 16.0 | 1.51872 | 0.00811 |
| | 0.0 | | | |
| | | 7.0 | 1 | 0 |
| Beam Rotating prism 64 | 0.0 | | | |
| | | 115.0 | 1.51872 | 0.00811 |
| | 0.0 | | | |
| | | 8.1666 | 1 | 0 |
| Relay lens 90 | 0.013784 | | | |
| | | 2.0 | 1.65222 | 0.019412 |
| | 0.045253 | | | |
| | | 8.0 | 1.54982 | 0.010309 |
| | −0.013076 | | | |
| | | 115.771 | 1 | 0 |
| Eyepiece lens 92 | −0.001984 | | | |
| | | 1.8025 | 1.62991 | 0.01775 |
| | 0.043517 | | | |
| | | 4.6299 | 1.52583 | 0.010267 |
| | −0.036657 | | | |
| | | 0.94272 | 1 | 0 |
| Eyepiece lens 94 | 0.002787 | | | |
| | | 4.8084 | 1.52583 | 0.010267 |
| | −0.071751 | | | |
| | | 1.9813 | 1.65222 | 0.019412 |
| | −0.031496 | | | |

TABLE I-continued

| Component | c(mm⁻¹) | d(mm) | n | v |
|---|---|---|---|---|
|  |  |  | 1 | 0 |

The dual viewing system may be used either with a human second observer or in conjunction with a still camera, cine camera or television camera.

Instead of a cystoscope, any other endoscope such as a laparoscope could be used, or any other image-forming optical instrument such as a periscope.

Figure 3:
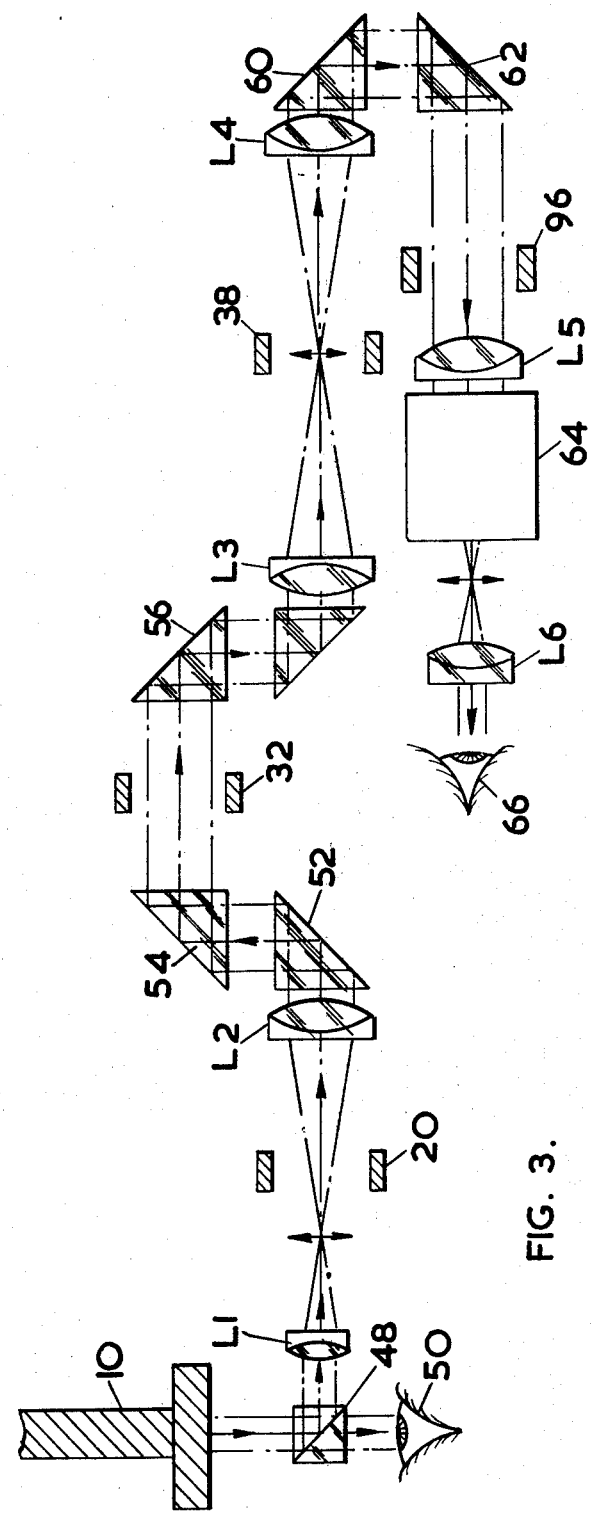
FIG. 3 illustrates schematically a simpler alternative embodiment to that shown in FIGS. 2A and 2B.

A simpler alternative embodiment of the invention is illustrated in FIG. 3, in which the number references correspond to those of FIGS. 1, 2A and 2B. This embodiment is simpler in that fewer lens elements are required, viz. six, $L_1$ to $L_6$, arranged as three telescopic arrangements $(L_1 + L_2)$, $(L_3 + L_4)$ and $(L_5 + L_6)$, as compared with 13 in the embodiment already described. An additional coaxial joint 96 can be included for extra flexibility. The principle is the same for both embodiments, but the simpler one can be used only up to a smaller maximum aperture. Where the working conditions render the smaller aperture acceptable the embodiment of FIG. 3 is to be preferred on grounds of lower weight and cost.

I claim:

1. A dual viewing optical system, for attachment to an optical instrument, comprising beam splitting means providing first and second beams of light, a first viewing position at which the first beam can be viewed, a first tube attached to the beam splitting means along which the second beam passes, the said first tube having a coaxial joint intermediate its ends which provides coaxial relative rotation of the ends of said first tube, a second tube having a coaxial joint intermediate its ends which provides coaxial relative rotation of the ends of said second tube, a first swivel joint connecting adjacent ends of said first and second tubes for rotation relatively to one another about the axis of said first swivel joint in parallel planes passing through the axes of said tubes, a remote eyepiece, means including a second swivel joint connecting said eyepiece to the end of said second tube remote from said first swivel joint, whereby the remote eyepiece may lie in any spatial direction relative to the direction of the first beam, and optical means to relay the second beam to the remote eyepiece.

2. A system according to claim 1 having additionally between the second swivel joint and the remote eyepiece a third tube, having a coaxial joint intermediate its ends, and a third swivel joint.

3. A system according to claim 1 wherein the optical means to relay the second beam to the remote eyepiece includes at least one lens arranged in the first tube and reflecting means arranged in the first swivel joint.

4. A system according to claim 3 wherein the reflecting means comprises two parallel mirrors.

5. A system according to claim 3 wherein the reflecting means comprises two reflecting prisms.

6. A system according to claim 2 having at least one lens in each tube, and two co-operating reflecting surfaces in each swivel joint arranged to reflect any beam passing axially along a preceding tube to pass axially along any succeeding tube and to the remote eyepiece.

7. A system according to claim 6 in which the lenses are arranged as a telescope in each tube to provide a sharp optical image at each swivel joint.

8. A system according to claim 6 in which the lenses are arranged as a telescope.

9. A system according to claim 8 in which the lenses are arranged as a telescope in each tube with an image at infinity in each swivel joint between the two reflecting surfaces in said joint.

10. A system according to claim 9 in which the lens system in the first tube has an angular magnification of less than one, the lens system in the second tube has an angular magnification numerically equal to one, and the lens system in the third tube has an angular magnification numerically greater than one.

11. A system according to claim 10 in which the angular magnification of the lens system in the third tube is the reciprocal of the angular magnification of the lens system in the first tube, whereby an observer at the remote eyepiece sees an image of the same size as that seen at the first viewing position.

12. A system according to claim 11 in which the angular magnifications are 2 and ½ respectively.

13. A system according to claim 1 having an even number of reflecting surfaces in the path of the second beam whereby an image observable at the remote eyepiece is congruent with the image observable at the first viewing position.

14. A system according to claim 1 having magnifying means for viewing an image at the first viewing position.

15. A system according to claim 1 in which the said optical instrument is an endoscope and in which a required image is provided at the beam splitting means.

16. A system according to claim 1 having an image-rotating prism, arranged adjacent the remote eyepiece, whereby any image can be rotated about the optical axis of the second beam.

* * * * *